US007122346B2

(12) United States Patent
Burckhardt et al.

(10) Patent No.: US 7,122,346 B2
(45) Date of Patent: Oct. 17, 2006

(54) PROCESS FOR THE RECOMBINANT PRODUCTION OF RIBONUCLEOPROTEINS

(75) Inventors: Jean Burckhardt, Magden (CH); Michael Haass, Neuenburg (DE); Hans-Peter Lehmann, Penzberg (DE)

(73) Assignee: F. Hoffmann-La Roche AG, Basel (CH)

(*) Notice: Subject to any disclaimer, the term of this patent is extended or adjusted under 35 U.S.C. 154(b) by 489 days.

(21) Appl. No.: 10/288,858

(22) Filed: Nov. 6, 2002

(65) Prior Publication Data

US 2003/0109001 A1 Jun. 12, 2003

Related U.S. Application Data

(63) Continuation of application No. 09/611,941, filed on Jul. 7, 2000, now abandoned.

(51) Int. Cl.
*C12P 21/06* (2006.01)
*C12N 1/20* (2006.01)
*C07H 21/02* (2006.01)
*C07H 21/04* (2006.01)
*C07K 14/00* (2006.01)

(52) U.S. Cl. .................. 435/69.1; 435/71.1; 435/252.3; 435/320.1; 536/23.1; 536/23.5; 530/350

(58) Field of Classification Search ............... 435/69.1, 435/252.3, 320.1, 455, 71.2; 536/23.1, 23.5; 530/350
See application file for complete search history.

(56) References Cited

OTHER PUBLICATIONS

Wells, Biochemistry, vol. 29, pp. 8509-8517, 1990.*
Gilles Boire et al., "Sera from Patients with Autoimmune Disease Recognize Conformational Determination the 60-kd Ro/SS-A Protein" Arthritis and Rheumatism, vol. 34, No. 6 (Jun. 1991) pp. 722-730.
Pascal Bouffard et al., "Anti-Ro (SSA) Antibodies: Clinical Significance and Biological Relevance" The Journal of Rheumatology 1996: 23:11 pp. 1838-1841.
Susan L. Deutscher et al., "Molecular Analysis of the 60-kDa Human Ro Ribonucleoprotein" Proc. Natl. Acad. Sci. USA vol. 85, pp. 9479-9483, Dec. 1988 Biochemistry.
Keith B. Elkon et al., "Partial Immunochemical Characterization of the Ro and La Proteins using Antibodies from Patients with the SICCA Syndrome and Lupus Erythernatosus" The Journal of Immunology Copyright 1984 by The American Association of Immunologists vol. 132. No. 5, May 1984 pp. 2350-2356.
A. Darise Farris et al., "Conserved Features of Y RNAs revealed by Automated Phylogenetic Secondary Structure Analysis" pp. 1070-1078 Nucleic Acids Research, 1999, vol. 27, No. 4, 1999 Oxford University Press.

(Continued)

*Primary Examiner*—Robert A. Wax
*Assistant Examiner*—Rita Mitra
(74) *Attorney, Agent, or Firm*—Barnes & Thornburg LLP

(57) ABSTRACT

A process is described for the recombinant production of ribonucleoproteins in prokaryotic cells.

20 Claims, 8 Drawing Sheets

OTHER PUBLICATIONS

Figure 5:
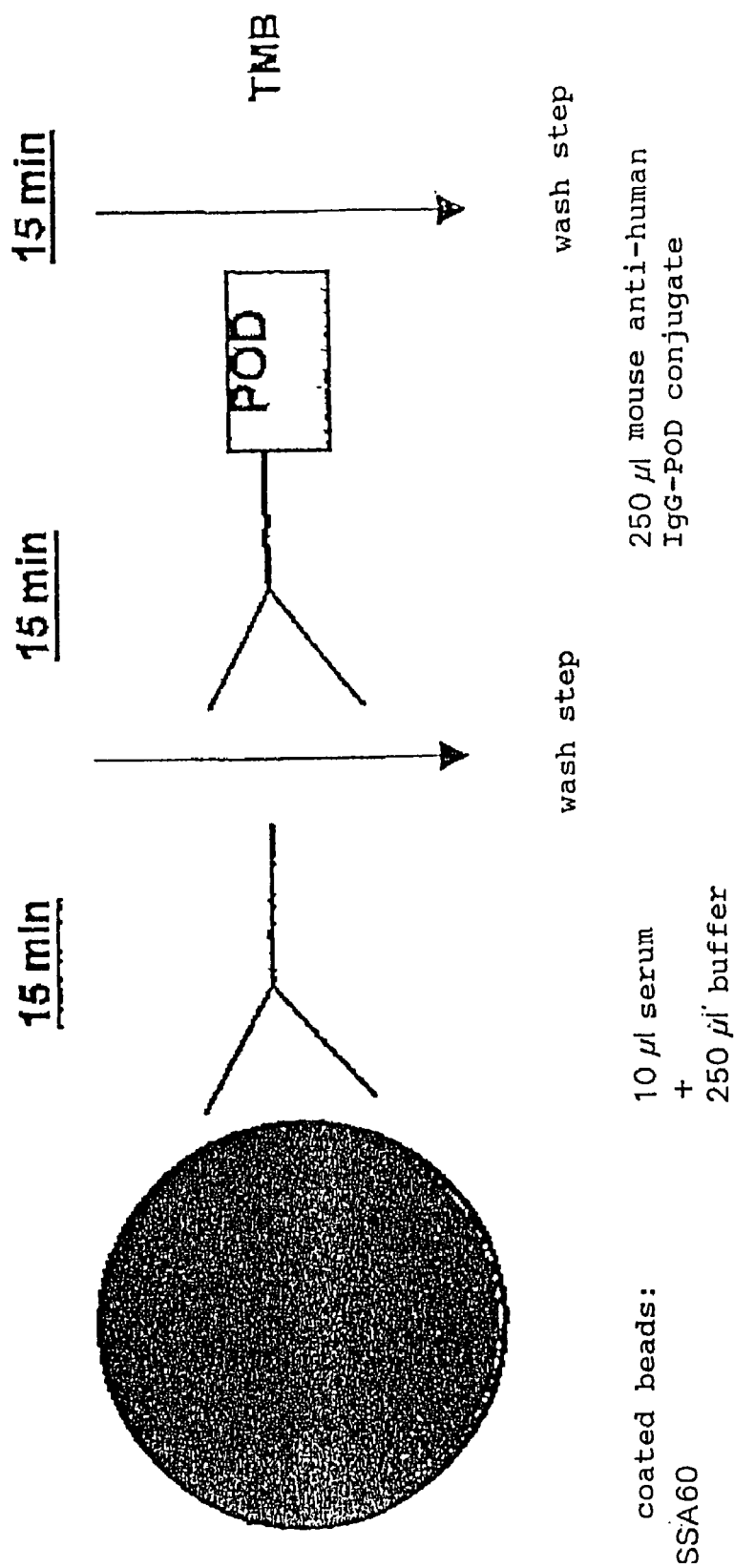

D. Granger et al., "RNA-labelled Ro and La Ribonucleoprotein Complexes Ressembled in Vitro; Characterization by Gel Shift Analysis" Clin. Exp Immunol 1996: 106:498 503, 1996 Blackwell Science pp. 498-503.

R. Humbel et al., "Identification and Characterisation of Anti-Nuclear and Anti-Cytoplasmatic Antibodies by Counterelectrophoresis" Arztl. Lab. 28 113-116 (1982).

Jose Gerardo Garcia Lerma et al., "Evaluation of Recombinant Ro/SSA, La/SSB, Sm, and U1 RNP Autoantigens in Clinical Diagnosis" Journal of Clinical Laboratory Analysis 9:52-58 (1995) pp. 52-58.

E. William St. Clair et al., "Specificity of Autoantibodies for Recombinant 60-kd and 52-kd Ro Autoantigens" Arthritis & Rheumatism vol. 37, No. 9, Sep. 1994 pp. 1373-1379, 1994 American College of Rheumatology.

C.H.A. Veldhoven et al., "The Development of a Quantitative Assay for the Detection of Anti-Ro/SS-A and anti-LA/SS-B Autoantibodies using Purified Recombinant Proteins" Journal of Immunological Methods, 151 (1992) 177-189 1992 Elsevier Science Publishers B.V.

Dunrul Wang et al., "Cloning and Expression of Mouse 60 kDa Ribonucleoprotein SS-A/Ro" Molecular Biology Reports 23: 205-210, 1996.

Dong-Hai Wu et al., "A Simple Method for the Biochemical Purification of Ro/SS-A Antigen" Journal of Immunological Methods, 121 (1989) 219-224 Elsevier.

Arth. Rheum. 1997, vol. 40, 1750-1755 p. S323.

* cited by examiner

Fig. 1 upper amino acid sequence: SSA60 M4-C6  SEQ ID NO: 1
lower amino acid sequence: SSA60 M56    SEQ ID NO: 2

```
  1 ......MRGSHHHHHG...SMEESVNQMQPLNEKQIANSQDGYVWQVTD
        ||||||||||||   |||||||||||||||||||||||||||||
        MRGSHHHHHGDDDDKESSVNQMQPLNEKQIANSQDGYVWQVTD

42 MNRLHRFLCFGSEGGTYYIKEQKLGLENAEALIRLIEDGRGCEVIQEIKS
    |||||||||||||||||||||||||||||||||||||||||||||||||
    MNRLHRFLCFGSEGGTYYIKEQKLGLENAEALIRLIEDGRGCEVIQEIKS

92 FSQEGRTTKQEPMLFALAICSQCSDISTKQAAFKAVSEVCRIPTHLFTFI
    |||||||||||||||||||||||||||||||||||||||||||||||||
    FSQEGRTTKQEPMLFALAICSQCSDISTKQAAFKAVSEVCRIPTHLFTFI

142 QFKKDLKESMKCGMWGRALRKAIADWYNEKGGMALALAVTKYKQRNGWSH
    |||||||||||||||||||||||||||||||||||||||||||||||||
    QFKKDLKESMKCGMWGRALRKAIADWYNEKGGMALALAVTKYKQRNGWSH

192 KDLLRLSHLKPSSEGLAIVTKYITKGWKEVHELYKEKALSVETEKLLKYL
    |||||||||||||||||||||||||||||||||||||||||||||||||
    KDLLRLSHLKPSSEGLAIVTKYITKGWKEVHELYKEKALSVETEKLLKYL

242 EAVEKVKRTKDELEVIHLIEEHRLVREHLLTNHLKSKEVWKALLQEMPLT
    |||||||||||||||||||||||||||||||||||||||||||||||||
    EAVEKVKRTKDELEVIHLIEEHRLVREHLLTNHLKSKEVWKALLQEMPLT

292 ALLRNLGKMTANSVLEPGNSEVSLVCEKLCNEKLLKKARIHPFHILIALE
    |||||||||||||||||||||||||||||||||||||||||||||||||
    ALLRNLGKMTANSVLEPGNSEVSLVCEKLCNEKLLKKARIHPFHILIALE

342 TYKTGHGLRGKLKWRPDEEILKALDAAFYKTFKTVEPTGKRFLLAVDVSA
    |||||||||||||||||||||||||||||||||||||||||||||||||
    TYKTGHGLRGKLKWRPDEEILKALDAAFYKTFKTVEPTGKRFLLAVDVSA

392 SMNQRVLGSILNASTVAAAMCMVVTRTEKDSYVVAFSDEMVPCPVTTDMT
    |||||||||||||||||||||||||||||||||||||||||||||||||
    SMNQRVLGSILNASTVAAAMCMVVTRTEKDSYVVAFSDEMVPCPVTTDMT

442 LQQVLMAMSQIPAGGTDCSLPMIWAQKTNTPADVFIVFTDNETFAGGVHP
    |||||||||||||||||||||||||||||||||||||||||||||||||
    LQQVLMAMSQIPAGGTDCSLPMIWAQKTNTPADVFIVFTDNETFAGGVHP

492 AIALREYRKKMDIPAKLIVCGMTSNGFTIADPDDRGMLDMCGFDTGALDV
    |||||||||||||||||||||||||||||||||||||||||||||||||
    AIALREYRKKMDIPAKLIVCGMTSNGFTIADPDDRGMLDMCGFDTGALDV

542 IRNFTLDMIVD**
    |||||||||
    IRNFTLDMI**
```

Fig. 2 upper nucleic acid sequence: HY3 (Wolin et al.) SEQ ID NO: 3
lower nucleic acid sequence: HY3 aus HY3-SSA60M56 SEQ ID NO: 4

```
  1 .............................................GGCTGGTCC   9
                                                 |||||||||
251 TTTATTTGCTTTGTGAGCGGATAACAATTATAATAGATTCAGGCTGGTCC       300

10 GAGTGCAGTGGTGTTTACAACTAATTGATCACAACCAGTTACAGATTTCT        59
    ||||||||||||||||||||||||||||||||||||||||||||||||||
301 GAGTGCAGTGGTGTTTACAACTAATTGATCACAACCAGTTACAGATTTCT       350

60 TTGTTCCTTCTCCACTCCCACTGCTTCACTTGACTAGCCTTT........       101
    |||||||||| |||||||||||||||||||||||||||||||
351 TTGTTCCTTCTTCACTCCCACTGCTTCACTTGACTAGCCTTTGCCGCCAG       400
```

Fig. 3

DNA and amino acid sequence of pEQ30-HY3-SSA60M56#4  SEQ ID NO: 5

```
        GCGACACGGAAATGTTGAATACTCATACTCTTCCTTTTTCAATATTATTGAAGCATTTAT
  1     ------------+---------+---------+---------+---------+---------+ 60
        CGCTGTGCCTTTACAACTTATGAGTATGAGAAGGAAAAAGTTATAATAACTTCGTAAATA

CAGGGTTATTGTCTCATGAGCGGATACATATTTGAATGTATTTAGAAAAATAAACAAATA
  61    ------------+---------+---------+---------+---------+---------+ 120
        GTCCCAATAACAGAGTACTCGCCTATGTATAAACTTACATAAATCTTTTTATTTGTTTAT

GGGGTTCCGCGCACATTTCCCCGAAAAGTGCCACCTGACGTCTAAGAAACCATTATTATC
  121   ------------+---------+---------+---------+---------+---------+ 180
        CCCCAAGGCGCGTGTAAAGGGGCTTTTCACGGTGGACTGCAGATTCTTTGGTAATAATAG

XhoI
                                                           |
        ATGACATTAACCTATAAAAATAGGCGTATCACGAGGCCCTTTCGTCTTCACCTCGAGAAA
  181   ------------+---------+---------+---------+---------+---------+ 240
        TACTGTAATTGGATATTTTTATCCGCATAGTGCTCCGGGAAAGCAGAAGTGGAGCTCTTT

TCATAAAAAATTTATTTGCTTTGTGAGCGGATAACAATTATAATAGATTCAGGCTGGTCC
  241   ------------+---------+---------+---------+---------+---------+ 300
        AGTATTTTTTAAATAAACGAAACACTCGCCTATTGTTAATATTATCTAAGTCCGACCAGG

GAGTGCAGTGGTGTTTACAACTAATTGATCACAACCAGTTACAGATTTCTTTGTTCCTTC
  301   ------------+---------+---------+---------+---------+---------+ 360
        CTCACGTCACCACAAATGTTGATTAACTAGTGTTGGTCAATGTCTAAAGAAACAAGGAAG

XhoI
                                                               |
        TTCACTCCCACTGCTTCACTTGACTAGCCTTTGCCGCCAGTTCCGCTGGCGGCATTTTCT
  361   ------------+---------+---------+---------+---------+---------+ 420
        AAGTGAGGGTGACGAAGTGAACTGATCGGAAACGGCGGTCAAGGCGACCGCCGTAAAAGA

CGAGAAATCATAAAAAATTTATTTGCTTTGTGAGCGGATAACAATTATAATAGATTCAAT
  421   ------------+---------+---------+---------+---------+---------+ 480
        GCTCTTTAGTATTTTTTAAATAAACGAAACACTCGCCTATTGTTAATATTATCTAAGTTA

EcoRI                                    BamHI
                  |                                        |
        TGTGAGCGGATAACAATTTCACACAGAATTCATTAAAGAGGAGAAATTAACCATGGGAGG
  481   ------------+---------+---------+---------+---------+---------+ 540
        ACACTCGCCTATTGTTAAAGTGTGTCTTAAGTAATTTCTCCTCTTTAATTGGTACCCTCC

M  G  G  -

ATCCCATCACCATCACCATCACGGTGATGACGATGACAAAGAGGAATCTGTAAACCAAAT
  541   ------------+---------+---------+---------+---------+---------+ 600
        TAGGGTAGTGGTAGTGGTAGTGCCACTACTGCTACTGTTTCTCCTTAGACATTTGGTTTA

S  H  H  H  H  H  H  G  D  D  D  D  K  E  E  S  V  N  Q  M  -
```

Fig. 3 (continued)

```
        GCAGCCACTGAATGAGAAGCAGATAGCCAATTCTCAGGATGGATATGTATGGCAAGTCAC
601     ------------+----------+----------+----------+----------+  660
        CGTCGGTGACTTACTCTTCGTCTATCGGTTAAGAGTCCTACCTATACATACCGTTCAGTG

Q  P  L  N  E  K  Q  I  A  N  S  Q  D  G  Y  V  W  Q  V  T  -

TGACATGAATCGACTACACCGGTTCTTATGTTTCGGTTCTGAAGGTGGGACTTATTATAT
661     ------------+----------+----------+----------+----------+  720
        ACTGTACTTAGCTGATGTGGCCAAGAATACAAAGCCAAGACTTCCACCCTGAATAATATA

D  M  N  R  L  H  R  F  L  C  F  G  S  E  G  G  T  Y  Y  I  -

HindIII
                                        |
        CAAAGAACAGAAGTTGGGCCTTGAAAATGCTGAAGCTTTAATTAGATTGATTGAAGATGG
721     ------------+----------+----------+----------+----------+  780
        GTTTCTTGTCTTCAACCCGGAACTTTTACGACTTCGAAATTAATCTAACTAACTTCTACC

K  E  Q  K  L  G  L  E  N  A  E  A  L  I  R  L  I  E  D  G  -

CAGAGGATGTGAAGTGATACAAGAAATAAAGTCATTTAGTCAAGAAGGCAGAACCACAAA
781     ------------+----------+----------+----------+----------+  840
        GTCTCCTACACTTCACTATGTTCTTTATTTCAGTAAATCAGTTCTTCCGTCTTGGTGTTT

R  G  C  E  V  I  Q  E  I  K  S  F  S  Q  E  G  R  T  T  K  -

GCAAGAGCCTATGCTCTTTGCACTTGCCATTTGTTCCCAGTGCTCCGATATCAGCACAAA
841     ------------+----------+----------+----------+----------+  900
        CGTTCTCGGATACGAGAAACGTGAACGGTAAACAAGGGTCACGAGGCTATAGTCGTGTTT

Q  E  P  M  L  F  A  L  A  I  C  S  Q  C  S  D  I  S  T  K  -

ACAAGCAGCATTCAAGGCTGTTTCTGAAGTTTGTCGCATTCCTACCCATCTCTTTACTTT
901     ------------+----------+----------+----------+----------+  960
        TGTTCGTCGTAAGTTCCGACAAAGACTTCAAACAGCGTAAGGATGGGTAGAGAAATGAAA

Q  A  A  F  K  A  V  S  E  V  C  R  I  P  T  H  L  F  T  F  -

TATCCAGTTTAAGAAAGACCTGAAGGAAAGCATGAAATGTGGCATGTGGGGTCGTGCCCT
961     ------------+----------+----------+----------+----------+
        ATAGGTCAAATTCTTTCTGGACTTCCTTTCGTACTTTACACCGTACACCCCAGCACGGGA

I  Q  F  K  K  D  L  K  E  S  M  K  C  G  M  W  G  R  A  L  -

CCGGAAGGCTATAGCGGACTGGTACAATGAGAAAGGTGGCATGGCCCTTGCTCTGGCAGT
1021    ------------+----------+----------+----------+----------+
        GGCCTTCCGATATCGCCTGACCATGTTACTCTTTCCACCGTACCGGGAACGAGACCGTCA

R  K  A  I  A  D  W  Y  N  E  K  G  G  M  A  L  A  L  A  V  -

BglII
                                        |
        TACAAAATATAAACAGAGAAATGGCTGGTCTCACAAAGATCTATTAAGATTGTCACATCT
1081    ------------+----------+----------+----------+----------+
        ATGTTTTATATTTGTCTCTTTACCGACCAGAGTGTTTCTAGATAATTCTAACAGTGTAGA

T  K  Y  K  Q  R  N  G  W  S  H  K  D  L  L  R  L  S  H  L  -
```

Fig. 3 (continued)

```
         TAAACCTTCCAGTGAAGGACTTGCAATTGTGACCAAATATATTACAAAGGGCTGGAAAGA
1141     ---------+---------+---------+---------+---------+---------+
         ATTTGGAAGGTCACTTCCTGAACGTTAACACTGGTTTATATAATGTTTCCCGACCTTTCT

K  P  S  S  E  G  L  A  I  V  T  K  Y  I  T  K  G  W  K  E  -

AGTTCATGAATTGTATAAAGAAAAAGCACTCTCTGTGGAGACTGAAAAATTATTAAAGTA
1201     ---------+---------+---------+---------+---------+---------+
         TCAAGTACTTAACATATTTCTTTTTCGTGAGAGACACCTCTGACTTTTTAATAATTTCAT

V  H  E  L  Y  K  E  K  A  L  S  V  E  T  E  K  L  L  K  Y  -

TCTGGAGGCTGTAGAGAAAGTGAAGCGCACAAAAGATGAGCTAGAAGTCATTCATCTAAT
1261     ---------+---------+---------+---------+---------+---------+
         AGACCTCCGACATCTCTTTCACTTCGCGTGTTTTCTACTCGATCTTCAGTAAGTAGATTA

L  E  A  V  E  K  V  K  R  T  K  D  E  L  E  V  I  H  L  I  -

AGAAGAACATAGATTAGTTAGAGAACATCTTTTAACAAATCACTTAAAGTCTAAAGAGGT
1321     ---------+---------+---------+---------+---------+---------+
         TCTTCTTGTATCTAATCAATCTCTTGTAGAAAATTGTTTAGTGAATTTCAGATTTCTCCA

E  E  H  R  L  V  R  E  H  L  L  T  N  H  L  K  S  K  E  V  -

ATGGAAGGCTTTGTTACAAGAAATGCCGCTTACTGCATTACTAAGGAATCTAGGAAAGAT
1381     ---------+---------+---------+---------+---------+---------+
         TACCTTCCGAAACAATGTTCTTTACGGCGAATGACGTAATGATTCCTTAGATCCTTTCTA

W  K  A  L  L  Q  E  M  P  L  T  A  L  L  R  N  L  G  K  M  -

GACTGCTAATTCAGTACTTGAACCAGGAAATTCAGAAGTATCTTTAGTATGTGAAAAACT
1441     ---------+---------+---------+---------+---------+---------+
         CTGACGATTAAGTCATGAACTTGGTCCTTTAAGTCTTCATAGAAATCATACACTTTTTGA

T  A  N  S  V  L  E  P  G  N  S  E  V  S  L  V  C  E  K  L  -

GTGTAATGAAAAACTATTAAAAAAGGCTCGTATACATCCATTTCATATTTTGATCGCATT
1501     ---------+---------+---------+---------+---------+---------+
         CACATTACTTTTTGATAATTTTTTCCGAGCATATGTAGGTAAAGTATAAAACTAGCGTAA

C  N  E  K  L  L  K  K  A  R  I  H  P  F  H  I  L  I  A  L  -
                                                       NarI
                                                        |
         AGAAACTTACAAGACAGGTCATGGTCTCAGAGGGAAACTGAAGTGGCGCCCTGATGAAGA
1561     ---------+---------+---------+---------+---------+---------+
         TCTTTGAATGTTCTGTCCAGTACCAGAGTCTCCCTTTGACTTCACCGCGGGACTACTTCT

E  T  Y  K  T  G  H  G  L  R  G  K  L  K  W  R  P  D  E  E  -

AATTTTGAAAGCATTGGATGCTGCTTTTTATAAAACATTTAAGACAGTTGAACCAACTGG
1621     ---------+---------+---------+---------+---------+---------+
         TTAAAACTTTCGTAACCTACGACGAAAAATATTTTGTAAATTCTGTCAACTTGGTTGACC

I  L  K  A  L  D  A  A  F  Y  K  T  F  K  T  V  E  P  T  G  -
```

Fig. 3 (continued)

```
         AAAACGTTTCTTACTAGCTGTTGATGTCAGTGCTTCTATGAACCAAAGAGTTTTGGGTAG
1681     ---------+---------+---------+---------+---------+---------+
         TTTTGCAAAGAATGATCGACAACTACAGTCACGAAGATACTTGGTTTCTCAAAACCCATC

K  R  F  L  L  A  V  D  V  S  A  S  M  N  Q  R  V  L  G  S  -

PstI
                           |
         TATACTCAACGCTAGTACAGTTGCTGCAGCAATGTGCATGGTTGTCACACGAACAGAAAA
1741     ---------+---------+---------+---------+---------+---------+
         ATATGAGTTGCGATCATGTCAACGACGTCGTTACACGTACCAACAGTGTGCTTGTCTTTT

I  L  N  A  S  T  V  A  A  A  M  C  M  V  V  T  R  T  E  K  -

KpnI
                                       |
         AGATTCTTATGTAGTTGCTTTTTCCGATGAAATGGTACCATGTCCAGTGACTACAGATAT
1801     ---------+---------+---------+---------+---------+---------+
         TCTAAGAATACATCAACGAAAAAGGCTACTTTACCATGGTACAGGTCACTGATGTCTATA

D  S  Y  V  V  A  F  S  D  E  M  V  P  C  P  V  T  T  D  M  -

GACCTTACAACAGGTTTTAATGGCTATGAGTCAGATCCCAGCGGGTGGAACTGATTGCTC
1861     ---------+---------+---------+---------+---------+---------+
         CTGGAATGTTGTCCAAAATTACCGATACTCAGTCTAGGGTCGCCCACCTTGACTAACGAG

T  L  Q  Q  V  L  M  A  M  S  Q  I  P  A  G  G  T  D  C  S  -

TCTTCCAATGATCTGGGCTCAGAAGACAAACACACCTGCTGATGTCTTCATTGTATTCAC
1921     ---------+---------+---------+---------+---------+---------+
         AGAAGGTTACTAGACCCGAGTCTTCTGTTTGTGTGGACGACTACAGAAGTAACATAAGTG

L  P  M  I  W  A  Q  K  T  N  T  P  A  D  V  F  I  V  F  T  -

TGATAATGAGACCTTTGCTGGAGGTGTCCATCCTGCTATTGCTCTGAGGGAGTATCGAAA
1981     ---------+---------+---------+---------+---------+---------+
         ACTATTACTCTGGAAACGACCTCCACAGGTAGGACGATAACGAGACTCCCTCATAGCTTT

D  N  E  T  F  A  G  G  V  H  P  A  I  A  L  R  E  Y  R  K  -

GAAAATGGATATTCCAGCTAAATTGATTGTTTGTGGAATGACATCAAATGGTTTCACCAT
2041     ---------+---------+---------+---------+---------+---------+
         CTTTTACCTATAAGGTCGATTTAACTAACAAACACCTTACTGTAGTTTACCAAAGTGGTA

K  M  D  I  P  A  K  L  I  V  C  G  M  T  S  N  G  F  T  I  -

SacI
                                                            |
         TGCAGACCCAGATGATAGAGGCATGTTGGATATGTGCGGCTTTGATACTGGAGCTCTGGA
2101     ---------+---------+---------+---------+---------+---------+
         ACGTCTGGGTCTACTATCTCCGTACAACCTATACACGCCGAAACTATGACCTCGAGACCT

A  D  P  D  D  R  G  M  L  D  M  C  G  F  D  T  G  A  L  D  -

TGTAATTCGAAATTTCACATTAGATATGATTTAATAGTCGAGCTTAATTAGCTGAGCTTG
2161     ---------+---------+---------+---------+---------+---------+
         ACATTAAGCTTTAAAGTGTAATCTATACTAAATTATCAGCTCGAATTAATCGACTCGAAC

V  I  R  N  F  T  L  D  M  I  *  *
```

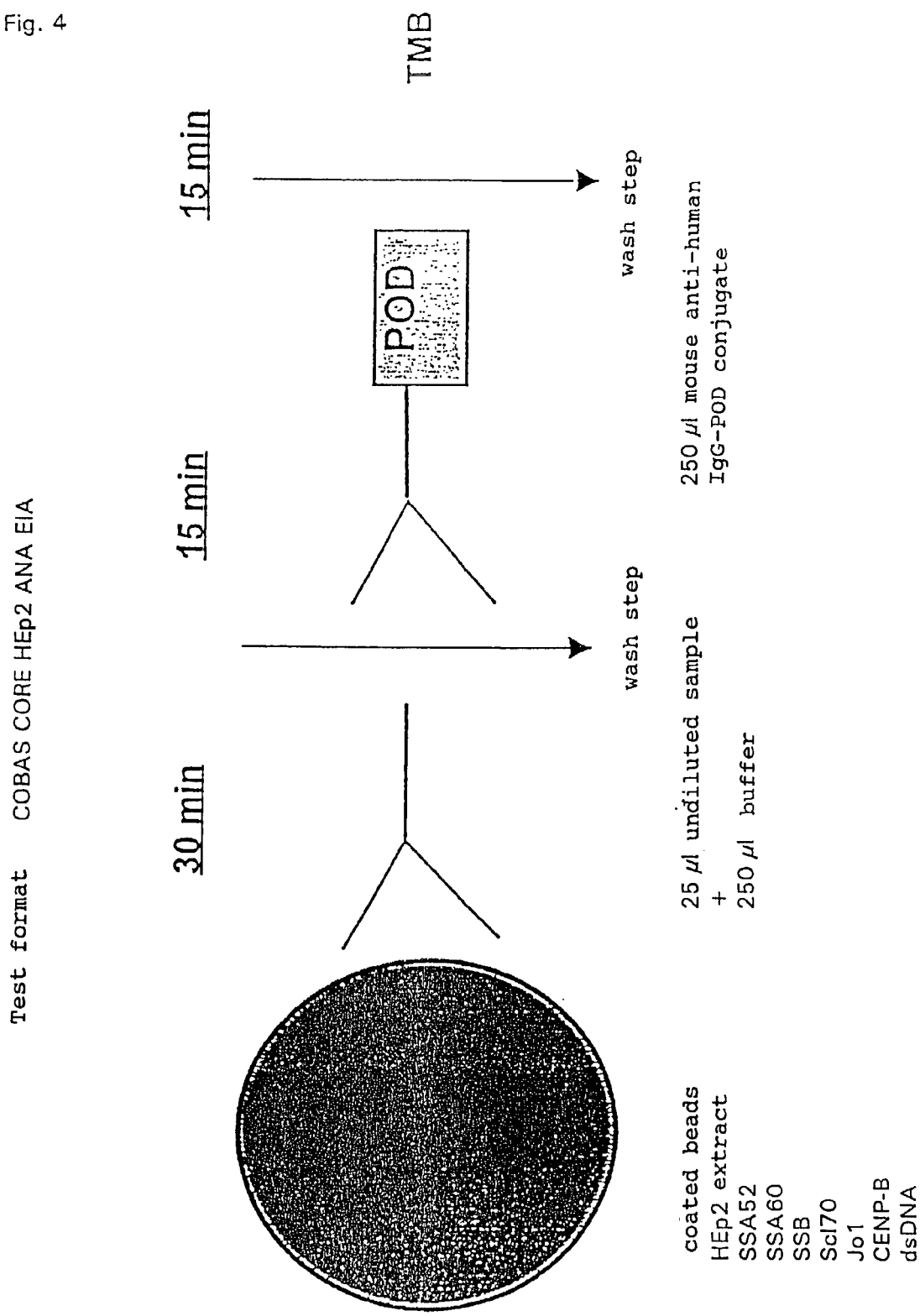

PROCESS FOR THE RECOMBINANT PRODUCTION OF RIBONUCLEOPROTEINS

CROSS REFERENCE TO RELATED APPLICATIONS

This application is a continuation application of U.S. patent application Ser. No. 09/611,941, filed on Jul. 7, 2000, now abandoned, and also claims foreign priority benefits under 35 U.S.C. §119 to German patent application no. 199 31 380.6 filed on Jul. 7, 1999.

The invention concerns a process for the recombinant production of a ribonucleoprotein in prokaryotic cells.

Antibodies frequently occur in the serum of patients with the autoimmune disease SLE (systemic lupus erythematosus) which are directed against ribonucleoproteins such as the SSA60 autoantigen. The SSA60 antigen is an RNA-binding molecule which occurs in the cytoplasm and in the nucleus of various cell types. The SSA60 antigen is often bound to a HY-RNA such as HY1, HY3, HY4 or HY5 which are each about 100 bases long and have a very similar structure. HY-RNA molecules which have been detected in many eukaryotic organisms do not occur in prokaryotes.

An analysis of the antibody response to ribonucleoproteins is of major interest in order to diagnose autoimmune diseases, in particular SLE, since the presence of antibodies directed against autoantigens indicates an existing autoimmune disease and/or allows a prognosis to be made for a possible future occurrence of an autoimmune disease.

The SSA60 antigen is often also referred to as SSA/Ro. It is a protein of about 60 kD in size. It is distinct from the SSA52 antigen with regard to its sequence as well as to its function although under certain in vivo conditions the SSA52 protein may be associated with the SSA60 protein.

The sequence of the cDNA of SSA60 was published by Deutscher et al., Proc. Natl. Acad. Sci. USA, Vol. 85 (1988), 9479–9483. HY-RNAs were described by Hendrick et al., J. Mol. Biol. 1 (1981), 1138–1149 as well as by Wolin et al., Proc. Natl. Acad. Sci. USA 81 (1984), 1996–2000.

Previously native purified SSA60 antigen (e.g. bovine spleen antigen from Immunovision) and pure recombinant SSA60 antigens from Baculovirus or *E. coli* have been used without RNA for diagnostic methods for example using an EIA (enzyme immunoassay) method. In this connection the three-dimensional structure (folding) of the antigen is of paramount importance for the immunological recognition of all relevant patient sera. The conformation and reproducibility of the SSA60 antigen varies depending on the production method as follows:

a) Native purified protein is the gold standard with regard to sensitivity for SSA60 autoantibodies (e.g. Immunovision). This material represents the physiological (native) conformation. However, false-positive results can occur when using this antigen e.g. by detecting natural autoantibodies which are not disease-relevant. In addition the reproducibility of the purification depends on the selection of the immunoaffinity matrix.

b) Recombinant protein from *E. coli* is essentially present in a denatured i.e. linear conformation since posttranslational modification of proteins does not occur in *E. coli*. As a result a certain proportion of patient sera are not detected. However, the detection of disease-relevant autoantibodies is more specific compared to the native antigen. A good reproducibility and yield can be obtained with this method. Recombinant free SSA60 antigen from *E. coli* which is not associated with RNA is used in this test procedure. For this purpose the cDNA of SSA60 is for example fished out of a cDNA bank, cloned and sequenced using primers that have been prepared according to the SSA60 sequence of Deutscher et al., supra. C. H. A. Veldhofen et al., J. Immunol. Methods 151 (1992) 177–189 describe the development of a quantitative assay for the detection of antibodies against SSA60 (RO/SSA) using recombinant free proteins which have been cloned and expressed in *E. coli*. However, it turned out that some sera that were identified as SSA60 positive with other tests were not detected with such antigen preparations without RNA since the antigens are present in a denatured form (G. Boire et al., Arthritis and Rheumatism, Vol. 34 No. 6 (1991), 722–730; B. William St. Clair et al., Arthritis and Rheumatism, Vol. 37 No. 9 (1994), 1373–1379).

c) Recombinant protein from Baculovirus can be regarded as pseudonative SSA60 antigen since in this eukaryotic expression system the folding occurs correctly during protein biosynthesis (at least the necessary disulfide bridge). The immunological reactivity is comparable with that of natively isolated SSA60 antigen. The problem with the production is the poor yield and the costly cell culture. Although good test results are achieved obtaining large amounts of autoantigens for commercial diagnostic methods using this process is very labour-intensive and has the problems associated with the handling of a cell culture.

Hence an object of the invention was to provide a process which is simple to carry out and can be used to obtain ribonucleoproteins in a form which gives a high sensitivity and test reliability in diagnostic procedures.

This object is achieved according to the invention by a process for the recombinant production of a ribonucleoprotein which comprises the steps:

(a) preparing a prokaryotic host cell which contains (i) at least one DNA coding for a ribonucleic acid component of the ribonucleoprotein and (ii) at least one DNA coding for a protein component of the ribonucleoprotein, (b) expressing the DNAs (i) and (ii) under such conditions that a ribonucleoprotein is formed and (c) isolating the ribonucleoprotein.

Surprisingly it was found that ribonucleoproteins can be prepared recombinantly in prokaryotic cells in a functional, e.g. immunologically active form, by concurrently expressing the ribonucleic acid and the protein component. This enables a simple and cost-effective production of ribonucleoproteins on a large scale. The protein and ribonucleic acid components are preferably obtained in an associated form. The ribonucleoproteins can be prepared in their native and thus usually soluble form. It has turned out that the sera from patients with SLE that are negative in tests with recombinantly produced proteins without a ribonucleic acid component could be detected with the ribonucleoproteins prepared according to the invention.

The process according to the invention is a very reproducible and cost-effective process for producing an SSA60 antigen with good immunological reactivity for the detection of disease-relevant SSA60 autoantibodies.

The ribonucleoproteins can be isolated from the prokaryotic cells or/and from the medium used to culture the cells. Gram-negative cells and in particular *E. coli* cells are preferably used.

The DNA coding for the ribonucleic acid component and the DNA coding for the protein component can be introduced into the prokaryotic host cell on a DNA construct. It is, however, also possible to introduce the DNAs coding for the individual components on separate DNA constructs. The method according to the invention can be used to produce any desired ribonucleoproteins, the protein component(s) and the corresponding nucleic acid component(s) being advantageously expressed in a host cell.

Preferably a eukaryotic, in particular a mammalian and particularly preferably a human ribonucleoprotein or a derivative thereof is produced. A derivative has a modified ribonucleic acid sequence and/or modified protein sequence compared to the native form for example by substitution, deletion, insertion or/and addition of individual or several amino acids or nucleobases while retaining the ability of the components to associate to form a ribonucleoprotein.

In a preferred embodiment an SSA60 ribonucleoprotein is expressed. The human SSA60 antigen is a protein with 525 (form a) and 538 (form b) amino acids (c.f. Deutscher et al., supra). A different splicing of the same primary transcript leads to the two different forms of the SSA60 protein. The two proteins only differ from amino acid 515 onwards whereas the amino acids 1 to 514 are constant. An SSA60 protein is preferably expressed using the method according to the invention which comprises the constant region of amino acids 1 to 514 and SSA60 protein derivatives with a modified sequence compared to the native form while retaining the antigen epitope properties.

The ribonucleic acid component is preferably a HY-RNA, in particular HY1, HY3, HY4 or/and HY5 and most preferably HY3. The HY-RNA molecules are highly conserved molecules with a very similar secondary structure. They are transcribed in vivo by polymerase III and have a size between 84 and 112 nucleotides.

Cytoplasmic RNA, in particular human RNA and preferably hY-RNA, makes an important contribution to the expression of the native conformation of the SSA60 antigen. The SSA60 antigen is present physiologically as a ribonucleoparticle (RNP) associated with SSB, SSA52 and hY-RNA.

A further aspect of the invention concerns a nucleic acid construct comprising a section which contains a DNA coding for a protein component and a section coding for a ribonucleic acid component. The coding sections are preferably in operative linkage with a sequence which enables the expression of the components in prokaryotic cells. The construct preferably contains a section containing a segment coding for an SSA60 protein or a derivative thereof. In a further preferred embodiment the construct contains a section coding for HY-RNA. A construct which contains a section coding for SSA60 and a section coding for HY3 is particularly preferred. When such a construct is expressed, an associated ribonucleoprotein is formed with the desired immunologically reactive conformation of the antigen. The association can be facilitated by simultaneously inducing the expression of ribonucleic acid component and protein component. This can be achieved by placing the gene for the ribonucleic acid component as well as the gene for the protein component under the control of the same regulatable expression systems e.g. lac expression systems.

A further aspect of the invention concerns a recombinant prokaryotic cell which contains (i) at least one DNA coding for a ribonucleic acid component of the ribonucleoprotein and (ii) at least one DNA coding for a protein component of the ribonucleoprotein. These coding regions can be present within the cell on a single construct or be separate on several constructs. The coding regions can be located extrachromosomally e.g. on plasmids or/and chromosomally.

A further subject matter of the invention is a recombinant ribonucleoprotein which is obtainable by the process described above. Coexpression of protein and ribonucleic acid in prokaryotic cells leads to the formation of a ribonucleoprotein which is not glycosylated and thus differs from ribonucleoproteins formed in eukaryotic host cells. The protein component of the recombinant ribonucleoprotein preferably contains heterologous auxiliary sequences which improve the expression or/and facilitate the purification. These auxiliary sequences can optionally contain protease cleavage sequences so that they can be removed after isolating the product. An example of an auxiliary sequence is a sequence section comprising several His residues (His tag).

A further subject matter of the invention is an SSA60 protein with the sequence SSA60M56 shown in FIG. 1. The SSA60 protein according to the invention has an auxiliary sequence at the N-terminus which, in addition to 6 His residues, contains a cleavage sequence DDDK for the proteolytic enzyme bovine enterokinase.

The invention additionally concerns the use of recombinant ribonucleoproteins from prokaryotes for diagnostic methods. The formation of ribonucleoproteins in a native and in particular in an associated form enable antigens to be provided which can be used to improve diagnostic methods. It is preferable to use a recombinant SSA60 ribonucleoprotein or a derivative thereof, especially together with HY3, for the diagnosis of autoimmune diseases e.g. SLE or Sjogren syndrome type A.

A further object of the invention is a method for the detection of an analyte in a sample using an analyte-specific receptor which is characterized in that a ribonucleoprotein as described herein is used as a receptor. The analyte is preferably an antibody to a ribonucleoprotein, for example an autoantibody like those which occur in autoimmune diseases. A suitable test procedure comprises the steps (a) preparing a solid phase which is coated with a ribonucleoprotein,
(b) contacting the coated solid phase with a sample and
(c) detecting a binding between the analyte and the coated solid phase.

Beads are used in particular as the solid phase, but other solid phases can also be used e.g. surfaces of reaction vessels or biochips. The solid phase can be coated only with the ribonucleoprotein or additionally with other molecules e.g. recombinant or/and native antigens or antigen mixtures. The ribonucleoproteins can be directly immobilized on the solid phase by adsorptive or covalent binding or they can be indirectly immobilized by means of a specific binding pair, in particular biotin/streptavidin, in which case the solid phase is firstly coated with one partner of the specific binding pair and then the ribonucleoprotein coupled to the second partner of the specific binding pair is applied to the precoated solid phase. The detection can be carried out in a conventional manner for example using a labelled antibody, in particular a mouse anti-human IgG POD (POD=peroxidase). Electrochemiluminescent labels, fluorescent labels, enzyme labels, sol particles such as e.g. latex particles or gold particles and radioactive labels are used in particular as marker groups.

The invention is further elucidated by the figures and the examples in which

FIG. 1 shows the amino acid sequence of the recombinant antigen SSA60 M4-C6 (upper sequence) and SSA60 M56 (lower sequence);

FIG. 2 shows a comparison of the sequence of HY3 (upper sequence) published by Wolin et al. in Proc. Natl. Acad. Sci. USA 81 (1984), 1996–2000 and the gene sequence used in the clone HY3-SSA60 M56 (lower sequence). The point mutation is indicated by the letter in bold type;

FIG. 3 shows the DNA and amino acid sequence of pQE30-HY3-SSA60 M56 #4, in which the HY3 gene is located between the two XhoI sites (bp 232–419) whereas the SSA60 M56 is located downstream of the EcoRI site (translation start at bp 533). Characteristic restriction sites are shown. The underlined amino acids are coded by the vector, the others are part of the human SSA60 sequence.

FIG. 4 shows a test format with coated beads where the beads can carry other detector molecules in addition to the ribonucleoproteins according to the invention such as a HEp2 extract, SSA52, SSA60, SSB, Scl70, Jo1, CENP-B or/and dsDNA. The coated beads are then incubated with undiluted sample e.g. 25 µl and a buffer e.g. 250 µl for example for 30 minutes. After a wash step, a detection reagent for example 250 ml mouse anti-human IgG POD conjugate is added and incubated for 15 minutes. Detection with TMB is carried out after a further wash step.

FIG. 5 shows a test format with beads which are coated with SSA60. The coated beads are incubated for 15 minutes with 10 µl serum as sample and 250 µl sample buffer. After a wash step, 250 µl mouse anti-human IgG POD conjugate is added and incubated for 15 minutes. Analysis with TMB is carried out after a further wash step.

EXAMPLE 1

Production of a Recombinant HY3-SSA60 Antigen

An antigen named SSA60-M56 was used which is a modified recombinant SSA60 protein with modifications at the N- and C-terminal ends which enables a recombinant protein to be produced with the amino acid sequence of the native SSA60 protein where no amino acids are coded by the vector and a recombinant SSA60 antigen which has a cleavable label only at the N-terminal end.

HY3 codes for a short RNA which associates with or binds to the recombinant SSA60 protein. The association of SSA60 with HY3 induces conformation epitopes of the antigen which leads to a different immunological behaviour compared to an SSA60 protein that contains no HY3-RNA. The two autoimmune antigens SSB and SSA60 bind to the same RNA molecule, whereas SSA52 is probably directly associated with the SSA60 protein.

The recombinant human SSA60 protein used in this case is the b form which is translated in the clone pQE30 HY3 SSA60 M56. It codes for a total of 553 amino acids. The first twelve amino acids at the N-terminal end of the protein are coded by the expression vector. This cleavable label contains a charged group of amino acids which increases the solubility of the antigen and it contains a group of six His for the affinity purification by means of Ni NTA.

The comparison shown in FIG. 1 of the amino acid sequence of the recombinant antigens SSA60 M4-C6 and SSA60 M56 shows that the N-terminal end of the recombinant SSA60 antigen was modified from MRGSHHHHH-HGSMEES . . . (SEQ ID NO: 15; sequence of a previously used clone) to MRGSHHHHHHGDDDDKEES. . . (SEQ ID NO: 16).

A DDDK sequence which is a cleavage sequence for the protease bovine enterokinase was inserted into the new sequence SSA60 M56 after the section containing 6 His amino acids. This enables the MRGSHHHHHHGDDDDK peptide (SEQ ID NO: 17) to be eliminated after purification of the antigen by means of Ni NTA. The C-terminal end of the recombinant antigen was changed from . . . IRNFTLD-MIVD (SEQ ID NO: 18; previously used clone) into . . . IRNFTLDMI (SEQ ID NO: 19). The asterisks mark the repetitive translation stop signals at the end of the protein. The sequence . . . . DMI represents the C-terminal end of the native and recombinant antigen.

HY3 is a small RNA with 101 bases and has a defined secondary structure. SSA60 binds to the base of the solid structure. The sequence used here differs in loop 2 of the RNA (see FIG. 2) compared to the structure of HY3 published in the prior art (Wolin et al., PNAS USA 81 (1984), 1996–2000).

The DNA sequence of the recombinant SSA60 protein and of the HY3-RNA gene is shown in FIG. 3. Characteristic restriction sites in the clone are indicated. Thus a restriction cleavage of the plasmid DNA of the clone PQE30 HY3 SSA60 M56 e.g. by XhoI, BglII and SacI results in four DNA fragments of 187 bp, 698 bp, 1038 bp and the vector (=3400 bp).

EXAMPLE 2

Construction of the Expression Vector

The expression vector pQE30 was used which is a small plasmid of 3462 bp (obtainable from Qiagen). This expression vector was specially designed for the expression of proteins in *E. coli*. It contains a regulatable promoter/operator element and a strong ribosome binding site in front of several cloning sites (BamHI and HindIII among others) which are located downstream of a group of 6 His. The expression of the gene under the control of the promoter/operator element is induced at a specified cell density by adding IPTG which inactivates the repressor and releases the promoter.

The recombinant plasmid pQE30 HY3 SSA60 M56, clone 4 results in an intracellular coexpression of the recombinant human SSA60 protein and the HY3-RNA in *E. coli*. These components together form a complex with conformation epitopes. The tag containing 6 His allows the purification of the antigen by metal chelate affinity chromatography. Non-denaturing purification conditions are necessary to retain the conformation epitopes of the-complex.

The lac repressor is coded by a separate plasmid which is named pREP4 which is compatible with the expression vector pDS56 RBSII. The plasmid pREP4 (from Qiagen) carries a kanamycin resistance factor whereas the expression vector is resistant to the antibiotic ampicillin.

The desired clone pQE30 HY3 SSA60 M56, clone 4 containing pREP4 is selected by culturing in the presence of the two antibiotics ampicillin and kanamycin.

In order to produce the clone pQE30 HY SSA60 M56, the HY3-RNA was firstly synthesised in vitro by PCR (polymerase chain reaction) using the primers HY3F and HY3R. The sequence of the primers was as follows:

Primer HY3-SynF:
5' ACTTGGTACCGAAATTAATACGACTCAC-TATAGGGAGAGGCTGGTCC GAGTGCAGTGGT-GTTTACAACTAATTGATCACAACCA 3' (SEQ ID NO: 7)

Primer HY3-SynR:
5' GTGTCTCGAGAAAGGCTA_TCAAGTGAAG-CAGTGGGAGTGGAGAAGG AACAAAGAAATCTG-TAACTGGTTGTGATCAATTAGTTG 3' (SEQ ID NO: 8)

Five 100 µl PCR reaction mixtures were prepared which contained 10 µl 10×Taq buffer (Pharmacia), 8 µl dNTP (1 mM dATP, dCTP, dGTP, dTTP), 3 µl of each of the primers HY3-SynF and HY3-SynR (50 pmol/µl each), 62 µl H₂O and 1 drop of mineral oil (Sigma, M-3516). A hot start was initiated in the first cycle at 60° C. with 10 µl (5 units Pharmacia Taq and 2.5 units Pfu [Stratagene] in 1×Taq buffer). The DNA amplification was carried out in a Perkin Elmer Cycler 9600 using the following programme:

1. Cycle 1
   30 seconds at 98° C.
   2 minutes at 60° C.
   30 seconds at 72° C.
2. Cycles 2 to 6
   30 seconds at 95° C.
   20 seconds at 65° C.
   30 seconds at 72° C.

The PCR fragments were collected, cleaved with the restriction enzymes XhoI and KpnI, purified by means of agarose gel and cloned into a Bluescript II KS vector whereby the gene HY3 was placed under the control of the T7 polymerase-promoter for transcription studies. This yielded the clone pBSII-HY3RNA3-1.

The expected sequence of the gene HY3 was found with the exception of a point mutation which is shown in FIG. 2. In vitro transcribed HY3-RNA was used to renature the SSA60 antigen which resulted in an increased positive immunological reactivity of the antigen.

In order to enable the synthesis of a recombinant SSA60 antigen without additional amino acids compared to the native sequence, vector-coded amino acids in the SSA60 clone that were used to coexpress SSA60 and HY3 were eliminated. The N-terminal end of the recombinant SSA60 antigen was modified for this to MRGSHHHHHHGD-DDDKEES . . . (SEQ ID NO: 16); clone SSA60-M56). The SSA60 protein begins in this case with the last three amino acids of this sequence i.e. EES . . . , whereas the remaining amino acids are coded by the vector. The sequence modification was obtained by a PCR reaction of a 260 bp fragment which covers the base pairs 506–758 of the SSA60-M56 sequence shown in FIG 3. The two primers SSA60 M6-NF and SSA60 M6-NRev had the following sequence:

1. SSA60 M6-NF
   5' cacagaattcattaaagaggagaaat-taactatgagaggatcccatcaccat-caccatcacggtgatgacgatgacaaagaggaatctg 3' (SEQ ID NO: 9)
2. SSA60 M6-NRev
   5' ctaattaaagcttcagcattttcaagg 3' (SEQ ID NO: 10)

The amplified DNA of 260 bp was cleaved and replaced the EcoRI/HindIII fragment of the clone SSA60-M4-C6. The sequence of the new clone is shown in FIG. 3.

The C-terminal end of the recombinant antigen was modified from . . . IRNFTLDMIVD (SEQ ID NO: 18; clone SSA60 M4-C6) into . . . IRNFTLDMI (SEQ ID NO: 19); clone SSA60 M56). The sequence modification was obtained by PCR reaction of a 260 bp fragment which comprised the bp 506–758 of the SSA60 M56 sequence shown in FIG. 3. The two primers SSA60M5-CF and SSA60M5-CRev had the following sequence:

1. SSA60M5-CF
   5' gatactggagctctggatgtaattc-gaaatttcacattagatatgatttaatagtcgcgagccagctt 3' (SEQ ID NO: 11)
2. SSA60M5-CRev
   5' aggcagctctagagcggcggatttgtcc 3'(SEQ ID NO: 12)

The amplified DNA of 1200 bp was cleaved with the restriction enzymes SacI and XbaI and the purified fragment was inserted into SSA60M4-C6 which replaced the previous fragment SacI-XbaI (the site of the fragment is shown in FIG. 3 downstream of SacI at bp 2155; XbaI is not shown since it is located in the vector pQE).

The clone obtained by these modifications was named pQE30-SSA60-M56#6. In order to differentiate between SSA60 and M56SSA60M4-CI the restriction site for SalI at the end of the SSA60 antigen was removed.

A clone was synthesized which coexpresses HY3 and SSA60 in *E. coli* and was named pQE30-HY3-SSA60M56#4. For this purpose HY3 was cloned in front of the SSA60 gene into the clone pQE30 SSA60M56#6 and the gene HY3 was placed under the control of the same promoter and operator sequences as for the SSA60 gene.

The HY3 gene was prepared for insertion into the XhoI site of pQE30 by modifying its sequence as described above with the aid of the primers HYFPQE and HYRPQE by PCR modification. The sequences of the two primers were:

HYFPQE
5' acttctcgagaaatcataaaaaatt-tatttgctttgtgagcggataacaattataatagattcaggctggtccgagtgcagt 3' (SEQ ID NO: 13)

HYRPQE
5' gtgtctcgagaaaatgccgccagcggaactggcggcaaaggctagtcaagtgaagcagtggg 3' (SEQ ID NO: 14)

The product of this reaction was cleaved with the restriction enzyme XhoI and cloned into the XhoI site of the clone pQE30 SSA60 M56 #6 which yielded the new clone pQE30-HY3-SSA60M56#4. The DNA and protein sequence of the new clone are shown in FIG. 3.

EXAMPLE 3

Expression of pQE30-HY3-SSA60M56, Clone 4

The *E. coli* strain used to overexpress the recombinant ribonucleoprotein complex HY3-SSA60 is an *E. coli* C derivative named XL1 Blue (Stratagene). For the overexpression of the recombinant HY3-SSA60 complex a culture of pQE30-HY3-SSA60M56#4 in XL1 containing pREP4 is cultured at 28° C. in a selective TB medium (containing ampicillin and kanamycin). At about 25% of the maximum cell density a transcription and translation of the recombinant protein is induced with 1 mM IPTG and the washing is continued for 3 to 5 hours at 28° C. Bacterial pellets which contain the recombinant protein are collected by centrifugation and the cell pellet is stored frozen until purification of the overexpressed recombinant antigen.

An optimization of the expression of immunologically reactive material shows that especially the combination of 1.) fermentation at a low temperature and 2.) non-denaturing purification protocols gave satisfactory results.

In order to monitor the overexpression of the HY3-SSA60 antigen, protein aliquots of the induced bacteria were stained after electrophoresis on an SDS polyacrylamide gel. The recombinant HY3-SSA60 antigen migrates as a major protein band at 75 kD compared to prestained Seablue marker (Novex # LC 5625).

EXAMPLE 4

Native Purification of the Coexpressed HY3-RNA-SSA60 Construct

A mixture of 1 mM PMSF (prepared from 0.2 M PMSF in 2-propanol), aprotinin (10 mg/ml in water) in an amount of 10 μg/g biomass, leupeptin (1 mg/ml in water) in an amount of 15 μg/g biomass, pepstatin (1 mg/ml in methanol)

in an amount of 15 µg/g biomass and lysozyme (10 mg/ml in lysis buffer) in an amount of 100 µl/g biomass was used as the extraction buffer. The buffer was added at room temperature while adhering to an extraction ratio of 1 g biomass/5 ml buffer comprising 10 mM Tris, pH 7.0, 500 mM NaCl, 10% glycerol and 0.2% Tween 20. The suspension was treated with ultrasound in ice water for 10 minutes at 5 second intervals for the extraction. It was centrifuged at 4° C. for 10 minutes at 10,000 g. The desired ribonucleoprotein HY3-RNA-SSA60 is present in solution in the supernatant. The supernatant was treated with SDS-PAGE and Western Blot. Subsequently a nickel purification of the positive supernatants was carried out under native operating conditions using a column operating buffer which contained 10 mM TRIS, pH 7.0, 500 mM NaCl, 10% glycerol and 0.2% Tween 20. The elution was carried out with 5 mM, 10 mM, 20 mM, 50 mM and 100 mM imidazole in column buffer. The elution fractions were analysed by means of SDS-PAGE and Western Blot and the fractions containing the desired ribonucleoprotein were collected.

EXAMPLE 5

Use of the HY3-RNA-SSA60 Ribonucleoprotein in a Diagnostic Method

The Cobas Core anti-SSA60 EIA test format used for the SSA60 comparison experiment is shown in FIG. 5. It is comparable with the test format for the Cobas Core HEp2 ANA EIA (combi test, cf. FIG. 4) with the exception that SSA60 antigen was used for the coating.

1) Coating

SSA60 antigens were incubated for 14 to 16 h at room temperature (RT) in phosphate buffer containing 0.15 M NaCl (PBS) and 2 mM EDTA with gamma-irradiated polystyrene beads (NUNC, Denmark) until saturation (max. SSA60 binding capacity).

After washing the beads three times with PBS they were transferred to a 2% BSA/PBS solution to saturate free binding sites (2–3 h at room temperature (RT)). The SSA60 beads were subsequently dried under vacuum for 2 h at RT, transferred to special dry containers (Cobas Core) and stored at 4° C. until use.

2) Test Procedure (EIA Carried Out Automatically by Cobas Core)

10 µl serum sample plus 250 µl diluent plus SSA60 beads are incubated for 15 min at 37° C. Afterwards they are washed three times with deionized water and incubated with 250 µl mouse anti-human-IgG peroxidase for 15 minutes at 37° C. After again washing three times with deionized water they are incubated with the peroxidase substrate TMB for 15 min at 37° C. The evaluation was carried out by measuring the OD at 650 nm. The colour signal at OD 650 is proportional to the specific antibody concentration in the serum.

3) Sera

The tested sera are partly of commercial origin (serum A: BM69660, serum B: BM6020, serum C: BM 7529, serum D: BM69440, serum E: M48/4713) and partly of clinical origin (serum F: SS12). The latter is a very rare serum from a patient with Sjörgren's syndrome. The reactivity of SSA60 antibodies was tested with various commercially available tests (ELISA). The commercial tests either contained native or recombinant SSA60 antigen. All positive sera could be detected as positive with the coated native SSA60 antigen from Immunovision whereas some of the samples gave a negative test result with the coated pure SSA60 protein from *E. coli* (denatured). The latter samples were converted from negative to positive by the use of native purified hY3-RNA-SSA60 instead of denatured SSA60.

Hence the desired reactivity of the hY3-RNA-SSA60 antigen in the test was proven.

TABLE 1

| | Saturation coated SSA60 antigen | | | | | |
|---|---|---|---|---|---|---|
| Experiment | OD650 nm SSA60 | OD650 nm Immunovision | OD650 nm SSA60-hY3 | OD650/CutOff SSA60 | OD650/CutOff Immunovision | OD650/CutOff SSA60-hY3 |
| positive sera | | | | | | |
| serum A | 3.50 | 3.50 | 3.30 | 5.83 | 38.89 | 7.49 |
| diluted 1:10 | 0.98 | 3.50 | 1.41 | 1.63 | 38.89 | 3.20 |
| serum B | 2.55 | 3.50 | 3.50 | 4.24 | 38.89 | 7.85 |
| diluted 1:10 | 0.46 | 2.63 | 1.15 | 0.77 | 29.22 | 2.62 |
| serum C | 3.38 | 3.50 | 2.7B | 5.63 | 28.89 | 6.32 |
| serum D | 3.50 | 3.50 | 3.44 | 5.83 | 38.89 | 7.83 |
| diluted 1:10 | 0.44 | 3.50 | 1.67 | 0.73 | 38.89 | 3.80 |
| serum E | 0.50 | 3.50 | 3.46 | 0.84 | 38.89 | 7.87 |
| diluted 1:10 | 0.28 | 3.50 | 1.63 | 0.44 | 38.89 | 3.71 |
| serum F | 0.24 | 3.50 | 1.22 | 0.40 | 38.89 | 2.77 |
| blood donor sera | | | | | | |
| 1 | 0.14 | 0.05 | 0.07 | 0.24 | 0.54 | 0.17 |
| 2 | 0.10 | 0.14 | 0.17 | 0.16 | 1.56 | 0.38 |
| 3 | 0.13 | 0.06 | 0.05 | 0.22 | 0.63 | 0.11 |
| 4 | 0.35 | 0.06 | 0.14 | 0.59 | 0.67 | 0.33 |
| 5 | 0.23 | 0.06 | 0.09 | 0.38 | 0.66 | 0.20 |
| 6 | 0.07 | 0.06 | 0.06 | 0.12 | 0.67 | 0.15 |
| 7 | 0.05 | 0.05 | 0.05 | 0.08 | 0.60 | 0.11 |
| 8 | 0.04 | 0.05 | 0.02 | 0.07 | 0.50 | 0.04 |
| 9 | 0.06 | 0.05 | 0.28 | 0.10 | 0.51 | 0.63 |
| 10 | 0.12 | 0.05 | 0.20 | 0.19 | 0.51 | 0.45 |
| 11 | 0.08 | 0.06 | 0.15 | 0.13 | 0.69 | 0.34 |
| 12 | 1.11 | 0.07 | 0.10 | 1.85 | 0.76 | 0.23 |
| 13 | 0.62 | 0.08 | 0.09 | 1.04 | 0.86 | 0.20 |

TABLE 1-continued

|  | Saturation coated SSA60 antigen | | | | | |
|---|---|---|---|---|---|---|
| Experiment | OD650 nm SSA60 | OD650 nm Immunovision | OD650 nm SSA60-hY3 | OD650/CutOff SSA60 | OD650/CutOff Immunovision | OD650/CutOff SSA60-hY3 |
| 14 | 0.30 | 0.08 | 0.14 | 0.49 | 0.90 | 0.32 |
| 15 | 0.07 | 0.13 | 0.04 | 0.12 | 1.44 | 0.10 |
| 16 | 0.21 | 0.06 | 0.07 | 0.35 | 0.62 | 0.15 |
| 17 | 0.20 | 0.05 | 0.08 | 0.34 | 0.59 | 0.18 |
| blood donor | | | | | | |
| MW1 | 0.25 | 0.07 | 0.17 | | | |
| STA1 | 0.27 | 0.03 | 0.21 | | | |
| MWY1 + 1.5 × STA1 | 0.66 | 0.13 | 0.59 | | | |
| MW2 | 0.17 | 0.06 | 0.13 | | | |
| STA2 | 0.14 | 0.01 | 0.10 | | | |
| cutoff (>MW2 + 3 × STD2) | 0.6 | 0.09 | 0.44 | | | |

Table 1 shows the results for positive sera and negative sera (blood donor sera) which are obtained using SSA60 produced recombinantly in *E. coli* without RNA, SSA60 from Immunovision (native SSA60 from bovine spleen) and SSA60-hY3 produced according to the invention. These results show that the sensitivity of the SSA60-hY3 produced according to the invention is considerably higher than that of SSA60 without RNA. A sample was classified as negative when the OD650 nm/cutoff <1 and as positive when the OD650 nm/cutoff >1. As shown in the table the positive sera B (diluted 1:10), D (diluted 1:10), E (undiluted and diluted 1:10) and the clinical sample serum F that are classified as negative with SSA60 without RNA are correctly detected as positive with the SSA60-hY3 produced according to the invention.

In addition the SSA60-hY3 produced according to the invention also has a higher specificity than SSA60 without RNA or the SSA60 from Immunovision as shown in the second part of table 1. This lists the results of 17 blood donors (negative sera). Whereas two negative sera (No. 12 and 13 or No. 2 and 15 respectively) are classified as positive with SSA60 as well as with the SSA60 from Immunovision, all sera are correctly recognized as negative using the SSA60-hY3 produced according to the invention.

We claim:

1. A process for the recombinant production of a ribonucleoprotein comprising the steps of:
   a) providing a prokaryotic host cell, said host cell comprising a first DNA coding for a ribonucleic acid component of said ribonucleoprotein and a second DNA coding for a protein component of said ribonucleoprotein,
   b) expressing said first DNA and said second DNA under conditions such that said ribonucleoprotein is formed within the prokaryotic host cell, and
   c) isolating said ribonucleoprotein.

2. The process of claim 1, wherein said protein component comprising amino acids 17–550 of SEQ ID NO: 2.

3. The process of claim 1, wherein said protein component consists of amino acids 17–550 of SEQ ID NO: 2.

4. The process of claim 1, wherein said ribonucleic acid component is a human Y RNA.

5. The process of claim 4, wherein said HY-RNA is selected from the group consisting of human Y1 RNA, human Y3 RNA, human Y4 RNA and human Y5 RNA.

6. A purified nucleic acid construct comprising a first section comprising a DNA coding for a protein component of a eukaryotic ribonucleoprotein and a second section comprising a DNA coding for a ribonucleic acid component of a eukaryotic ribonucleoprotein.

7. The construct of claim 6, wherein said protein is an Sjogren syndrome type A protein comprising amino acids 17–550 of SEQ ID NO: 2.

8. The construct of claim 6, wherein said ribonucleic acid component is a human Y RNA.

9. The construct of claim 7, wherein said ribonucleic acid component is human Y3 RNA encoded by the nucleic acid sequence of SEQ ID NO: 4.RNA.

10. The construct of claim 6, wherein induction of said ribonucleic acid component and said protein component is simultaneous.

11. The construct of claim 6, wherein said DNA coding for a protein component of a eukaryotic ribonucleoprotein and said DNA coding for a ribonucleic acid component of a eukaryotic ribonucleoprotein are each linked operatively with a lac operator.

12. A recombinant prokaryotic cell comprising a first DNA coding for a ribonucleic acid component of a ribonucleoprotein and a second DNA coding for a protein component of said ribonucleoprotein.

13. A recombinant ribonucleoprotein produced by a process comprising:
   culturing a prokaryotic host cell, wherein the host cell comprises a first DNA coding for a ribonucleic acid component of said ribonucleoprotein and a second DNA coding for a protein component of said ribonucleoprotein,
   expressing said first DNA and said second DNA under conditions such that said ribonucleoprotein is formed within the host cell, and
   isolating said ribonucleoprotein.

14. The process of claim 1 wherein the first DNA encodes an RNA comprising the sequence of SEQ ID NO: 3 or SEQ ID NO: 4, and the second DNA encodes a protein comprising the sequence of SEQ ID NO: 2.

15. The construct of claim 6 wherein the DNA comprises the nucleic acid sequence of SEQ ID NO: 5.

16. The recombinant cell of claim 12 wherein the first DNA encodes a protein comprising amino acids 17–550 of SEQ ID NO: 2.

17. The recombinant cell of claim 16 wherein the second DNA encodes an RNA selected from the group consisting of human Y1, human Y3, human Y4 and human Y5 RNAs.

18. The recombinant cell of claim 17 wherein the second DNA encodes a human Y3 RNA and comprises the nucleic acid sequence of SEQ ID NO: 3 or SEQ ID NO: 4.

19. The recombinant cell of claim 12 wherein the host cell comprises a DNA sequence of SEQ ID NO: 5.

20. A recombinant ribonucleoprotein produced by a process comprising:
   co-expressing a first DNA coding for a ribonucleic acid component of said ribonucleoprotein and a second DNA coding for a protein component of said ribonucleoprotein under conditions such that said ribonucleoprotein is formed, and
   isolating said ribonucleoprotein.

* * * * *

SEQUENCE LISTING

```
<160> NUMBER OF SEQ ID NOS: 14

<210> SEQ ID NO 1
<211> LENGTH: 552
<212> TYPE: PRT
<213> ORGANISM: Homo sapiens
<220> FEATURE:
<221> NAME/KEY: misc_feature
<223> OTHER INFORMATION: SSA60 M4-C6

<400> SEQUENCE: 1

Met Arg Gly Ser His His His His His His Gly Ser Met Glu Glu Ser
1               5                   10                  15

Val Asn Gln Met Gln Pro Leu Asn Glu Lys Gln Ile Ala Asn Ser Gln
            20                  25                  30

Asp Gly Tyr Val Trp Gln Val Thr Asp Met Asn Arg Leu His Arg Phe
        35                  40                  45

Leu Cys Phe Gly Ser Glu Gly Gly Thr Tyr Tyr Ile Lys Glu Gln Lys
    50                  55                  60

Leu Gly Leu Glu Asn Ala Glu Ala Leu Ile Arg Leu Ile Glu Asp Gly
65                  70                  75                  80

Arg Gly Cys Glu Val Ile Gln Glu Ile Lys Ser Phe Ser Gln Glu Gly
                85                  90                  95

Arg Thr Thr Lys Gln Glu Pro Met Leu Phe Ala Leu Ala Ile Cys Ser
            100                 105                 110

Gln Cys Ser Asp Ile Ser Thr Lys Gln Ala Ala Phe Lys Ala Val Ser
            115                 120                 125
```

-continued

Glu Val Cys Arg Ile Pro Thr His Leu Phe Thr Phe Ile Gln Phe Lys
130                 135                 140

Lys Asp Leu Lys Glu Ser Met Lys Cys Gly Met Trp Gly Arg Ala Leu
145                 150                 155                 160

Arg Lys Ala Ile Ala Asp Trp Tyr Asn Glu Lys Gly Gly Met Ala Leu
                165                 170                 175

Ala Leu Ala Val Thr Lys Tyr Lys Gln Arg Asn Gly Trp Ser His Lys
                180                 185                 190

Asp Leu Leu Arg Leu Ser His Leu Lys Pro Ser Ser Glu Gly Leu Ala
                195                 200                 205

Ile Val Thr Lys Tyr Ile Thr Lys Gly Trp Lys Glu Val His Glu Leu
210                 215                 220

Tyr Lys Glu Lys Ala Leu Ser Val Glu Thr Glu Lys Leu Leu Lys Tyr
225                 230                 235                 240

Leu Glu Ala Val Glu Lys Val Lys Arg Thr Lys Asp Glu Leu Glu Val
                245                 250                 255

Ile His Leu Ile Glu Glu His Arg Leu Val Arg Glu His Leu Leu Thr
                260                 265                 270

Asn His Leu Lys Ser Lys Glu Val Trp Lys Ala Leu Leu Gln Glu Met
                275                 280                 285

Pro Leu Thr Ala Leu Leu Arg Asn Leu Gly Lys Met Thr Ala Asn Ser
290                 295                 300

Val Leu Glu Pro Gly Asn Ser Glu Val Ser Leu Val Cys Glu Lys Leu
305                 310                 315                 320

Cys Asn Glu Lys Leu Leu Lys Lys Ala Arg Ile His Pro Phe His Ile
                325                 330                 335

Leu Ile Ala Leu Glu Thr Tyr Lys Thr Gly His Gly Leu Arg Gly Lys
                340                 345                 350

Leu Lys Trp Arg Pro Asp Glu Glu Ile Leu Lys Ala Leu Asp Ala Ala
                355                 360                 365

Phe Tyr Lys Thr Phe Lys Thr Val Glu Pro Thr Gly Lys Arg Phe Leu
370                 375                 380

Leu Ala Val Asp Val Ser Ala Ser Met Asn Gln Arg Val Leu Gly Ser
385                 390                 395                 400

Ile Leu Asn Ala Ser Thr Val Ala Ala Ala Met Cys Met Val Val Thr
                405                 410                 415

Arg Thr Glu Lys Asp Ser Tyr Val Val Ala Phe Ser Asp Glu Met Val
                420                 425                 430

Pro Cys Pro Val Thr Thr Asp Met Thr Leu Gln Gln Val Leu Met Ala
                435                 440                 445

Met Ser Gln Ile Pro Ala Gly Gly Thr Asp Cys Ser Leu Pro Met Ile
450                 455                 460

Trp Ala Gln Lys Thr Asn Thr Pro Ala Asp Val Phe Ile Val Phe Thr
465                 470                 475                 480

Asp Asn Glu Thr Phe Ala Gly Gly Val His Pro Ala Ile Ala Leu Arg
                485                 490                 495

Glu Tyr Arg Lys Lys Met Asp Ile Pro Ala Lys Leu Ile Val Cys Gly
                500                 505                 510

Met Thr Ser Asn Gly Phe Thr Ile Ala Asp Pro Asp Asp Arg Gly Met
515                 520                 525

```
Leu Asp Met Cys Gly Phe Asp Thr Gly Ala Leu Asp Val Ile Arg Asn
    530                 535                 540

Phe Thr Leu Asp Met Ile Val Asp
545                 550

<210> SEQ ID NO 2
<211> LENGTH: 553
<212> TYPE: PRT
<213> ORGANISM: Homo sapiens
<220> FEATURE:
<221> NAME/KEY: misc_feature
<223> OTHER INFORMATION: SSA60 M56

<400> SEQUENCE: 2

Met Arg Gly Ser His His His His His His Gly Asp Asp Asp Lys
1               5                   10                  15

Glu Glu Ser Val Asn Gln Met Gln Pro Leu Asn Glu Lys Gln Ile Ala
                20                  25                  30

Asn Ser Gln Asp Gly Tyr Val Trp Gln Val Thr Asp Met Asn Arg Leu
            35                  40                  45

His Arg Phe Leu Cys Phe Gly Ser Gly Gly Thr Tyr Tyr Ile Lys
50                  55                  60

Glu Gln Lys Leu Gly Leu Glu Asn Ala Glu Ala Leu Ile Arg Leu Ile
65                  70                  75                  80

Glu Asp Gly Arg Gly Cys Glu Val Ile Gln Glu Ile Lys Ser Phe Ser
                85                  90                  95

Gln Glu Gly Arg Thr Thr Lys Gln Glu Pro Met Leu Phe Ala Leu Ala
            100                 105                 110

Ile Cys Ser Gln Cys Ser Asp Ile Ser Thr Lys Gln Ala Ala Phe Lys
            115                 120                 125

Ala Val Ser Glu Val Cys Arg Ile Pro Thr His Leu Phe Thr Phe Ile
130                 135                 140

Gln Phe Lys Lys Asp Leu Lys Glu Ser Met Lys Cys Gly Met Trp Gly
145                 150                 155                 160

Arg Ala Leu Arg Lys Ala Ile Ala Asp Trp Tyr Asn Glu Lys Gly Gly
                165                 170                 175

Met Ala Leu Ala Leu Ala Val Thr Lys Tyr Lys Gln Arg Asn Gly Trp
            180                 185                 190

Ser His Lys Asp Leu Leu Arg Leu Ser His Leu Lys Pro Ser Ser Glu
        195                 200                 205

Gly Leu Ala Ile Val Thr Lys Tyr Ile Thr Lys Gly Trp Lys Glu Val
    210                 215                 220

His Glu Leu Tyr Lys Glu Lys Ala Leu Ser Val Glu Thr Glu Lys Leu
225                 230                 235                 240

Leu Lys Tyr Leu Glu Ala Val Glu Lys Val Lys Arg Thr Lys Asp Glu
                245                 250                 255

Leu Glu Val Ile His Leu Ile Glu Glu His Arg Leu Val Arg Glu His
            260                 265                 270

Leu Leu Thr Asn His Leu Lys Ser Lys Glu Val Trp Lys Ala Leu Leu
        275                 280                 285

Gln Glu Met Pro Leu Thr Ala Leu Leu Arg Asn Leu Gly Lys Met Thr
    290                 295                 300

Ala Asn Ser Val Leu Glu Pro Gly Asn Ser Glu Val Ser Leu Val Cys
305                 310                 315                 320

Glu Lys Leu Cys Asn Glu Lys Leu Leu Lys Lys Ala Arg Ile His Pro
                325                 330                 335
```

```
Phe His Ile Leu Ile Ala Leu Glu Thr Tyr Lys Thr Gly His Gly Leu
                340                 345                 350
Arg Gly Lys Leu Lys Trp Arg Pro Asp Glu Glu Ile Leu Lys Ala Leu
            355                 360                 365
Asp Ala Ala Phe Tyr Lys Thr Phe Lys Thr Val Glu Pro Thr Gly Lys
        370                 375                 380
Arg Phe Leu Leu Ala Val Asp Val Ser Ala Ser Met Asn Gln Arg Val
385                 390                 395                 400
Leu Gly Ser Ile Leu Asn Ala Ser Thr Val Ala Ala Met Cys Met
                405                 410                 415
Val Val Thr Arg Thr Glu Lys Asp Ser Tyr Val Val Ala Phe Ser Asp
                420                 425                 430
Glu Met Val Pro Cys Pro Val Thr Thr Asp Met Thr Leu Gln Gln Val
                435                 440                 445
Leu Met Ala Met Ser Gln Ile Pro Ala Gly Gly Thr Asp Cys Ser Leu
                450                 455                 460
Pro Met Ile Trp Ala Gln Lys Thr Asn Thr Pro Ala Asp Val Phe Ile
465                 470                 475                 480
Val Phe Thr Asp Asn Glu Thr Phe Ala Gly Val His Pro Ala Ile
                485                 490                 495
Ala Leu Arg Glu Tyr Arg Lys Lys Met Asp Ile Pro Ala Lys Leu Ile
                500                 505                 510
Val Cys Gly Met Thr Ser Asn Gly Phe Thr Ile Ala Asp Pro Asp Asp
                515                 520                 525
Arg Gly Met Leu Asp Met Cys Gly Phe Asp Thr Gly Ala Leu Asp Val
                530                 535                 540
Ile Arg Asn Phe Thr Leu Asp Met Ile
545                 550

<210> SEQ ID NO 3
<211> LENGTH: 101
<212> TYPE: DNA
<213> ORGANISM: Homo sapiens
<220> FEATURE:
<221> NAME/KEY: misc_feature
<223> OTHER INFORMATION: HY3 (Wolin et al., PNAS 81 (1984), 1996-2000)

<400> SEQUENCE: 3
ggctggtccg agtgcagtgg tgtttacaac taattgatca caaccagtta cagatttctt    60
tgttccttct ccactcccac tgcttcactt gactagcctt t                       101

<210> SEQ ID NO 4
<211> LENGTH: 150
<212> TYPE: DNA
<213> ORGANISM: Homo sapiens
<220> FEATURE:
<221> NAME/KEY: misc_feature
<223> OTHER INFORMATION: HY3 from SSA60 M56

<400> SEQUENCE: 4
tttatttgct tgtgagcgg ataacaatta taatagattc aggctggtcc gagtgcagtg    60
gtgtttacaa ctaattgatc acaaccagtt acagatttct tgttccttc ttcactccca   120 ctgcttcact tgactagcct tgccgccag                                    150

<210> SEQ ID NO 5
<211> LENGTH: 2220
<212> TYPE: DNA
<213> ORGANISM: Homo sapiens
```

-continued

```
<220> FEATURE:
<221> NAME/KEY: CDS
<222> LOCATION: (533)..(2191)

<400> SEQUENCE: 5
gcgacacgga aatgttgaat actcatactc ttccttttc aatattattg aagcatttat    60
cagggttatt gtctcatgag cggatacata tttgaatgta tttagaaaaa taaacaaata   120
ggggttccgc gcacatttcc ccgaaaagtg ccacctgacg tctaagaaac cattattatc   180
atgacattaa cctataaaaa taggcgtatc acgaggccct ttcgtcttca cctcgagaaa   240
tcataaaaaa tttatttgct ttgtgagcgg ataacaatta taatagattc aggctggtcc   300
gagtgcagtg gtgtttacaa ctaattgatc acaaccagtt acagatttct ttgttccttc   360
ttcactccca ctgcttcact tgactagcct ttgccgccag ttccgctggc ggcattttct   420
cgagaaatca taaaaatt atttgctttg tgagcggata acaattataa tagattcaat    480
tgtgagcgga taacaatttc acacagaatt cattaaagag gagaaattaa cc atg gga   538
                                                         Met Gly
                                                           1
```

| | | | | | | | | | | | | | | | | |
|---|---|---|---|---|---|---|---|---|---|---|---|---|---|---|---|---|
| gga | tcc | cat | cac | cat | cac | cat | cac | ggt | gat | gac | gat | gac | aaa | gag | gaa | 586 |
| Gly | Ser | His | His | His | His | His | His | Gly | Asp | Asp | Asp | Asp | Lys | Glu | Glu | |
| | | 5 | | | | 10 | | | | | 15 | | | | | |

```
tct gta aac caa atg cag cca ctg aat gag aag cag ata gcc aat tct    634
Ser Val Asn Gln Met Gln Pro Leu Asn Glu Lys Gln Ile Ala Asn Ser
    20              25                  30 cag gat gga tat gta tgg caa gtc act gac atg aat cga cta cac cgg    682
Gln Asp Gly Tyr Val Trp Gln Val Thr Asp Met Asn Arg Leu His Arg
35              40                  45                  50 ttc tta tgt ttc ggt tct gaa ggt ggg act tat tat atc aaa gaa cag    730
Phe Leu Cys Phe Gly Ser Glu Gly Gly Thr Tyr Tyr Ile Lys Glu Gln
                55                  60                  65 aag ttg ggc ctt gaa aat gct gaa gct tta att aga ttg att gaa gat    778
Lys Leu Gly Leu Glu Asn Ala Glu Ala Leu Ile Arg Leu Ile Glu Asp
            70                  75                  80 ggc aga gga tgt gaa gtg ata caa gaa ata aag tca ttt agt caa gaa    826
Gly Arg Gly Cys Glu Val Ile Gln Glu Ile Lys Ser Phe Ser Gln Glu
        85                  90                  95 ggc aga acc aca aag caa gag cct atg ctc ttt gca ctt gcc att tgt    874
Gly Arg Thr Thr Lys Gln Glu Pro Met Leu Phe Ala Leu Ala Ile Cys
    100                 105                 110 tcc cag tgc tcc gat atc agc aca aaa caa gca gca ttc aag gct gtt    922
Ser Gln Cys Ser Asp Ile Ser Thr Lys Gln Ala Ala Phe Lys Ala Val
115                 120                 125                 130 tct gaa gtt tgt cgc att cct acc cat ctc ttt act ttt atc cag ttt    970
Ser Glu Val Cys Arg Ile Pro Thr His Leu Phe Thr Phe Ile Gln Phe
                135                 140                 145 aag aaa gac ctg aag gaa agc atg aaa tgt ggc atg tgg ggt cgt gcc   1018
Lys Lys Asp Leu Lys Glu Ser Met Lys Cys Gly Met Trp Gly Arg Ala
            150                 155                 160 ctc cgg aag gct ata gcg gac tgg tac aat gag aaa ggt ggc atg gcc   1066
Leu Arg Lys Ala Ile Ala Asp Trp Tyr Asn Glu Lys Gly Gly Met Ala
        165                 170                 175 ctt gct ctg gca gtt aca aaa tat aaa cag aga aat ggc tgg tct cac   1114
Leu Ala Leu Ala Val Thr Lys Tyr Lys Gln Arg Asn Gly Trp Ser His
    180                 185                 190 aaa gat cta tta aga ttg tca cat ctt aaa cct tcc agt gaa gga ctt   1162
Lys Asp Leu Leu Arg Leu Ser His Leu Lys Pro Ser Ser Glu Gly Leu
195                 200                 205                 210
```

```
                                                          -continued gca att gtg acc aaa tat att aca aag ggc tgg aaa gaa gtt cat gaa    1210
Ala Ile Val Thr Lys Tyr Ile Thr Lys Gly Trp Lys Glu Val His Glu
            215                 220                 225 ttg tat aaa gaa aaa gca ctc tct gtg gag act gaa aaa tta tta aag    1258
Leu Tyr Lys Glu Lys Ala Leu Ser Val Glu Thr Glu Lys Leu Leu Lys
        230                 235                 240 tat ctg gag gct gta gag aaa gtg aag cgc aca aaa gat gag cta gaa    1306
Tyr Leu Glu Ala Val Glu Lys Val Lys Arg Thr Lys Asp Glu Leu Glu
    245                 250                 255 gtc att cat cta ata gaa gaa cat aga tta gtt aga gaa cat ctt tta    1354
Val Ile His Leu Ile Glu Glu His Arg Leu Val Arg Glu His Leu Leu
260                 265                 270 aca aat cac tta aag tct aaa gag gta tgg aag gct ttg tta caa gaa    1402
Thr Asn His Leu Lys Ser Lys Glu Val Trp Lys Ala Leu Leu Gln Glu
275                 280                 285                 290 atg ccg ctt act gca tta cta agg aat cta gga aag atg act gct aat    1450
Met Pro Leu Thr Ala Leu Leu Arg Asn Leu Gly Lys Met Thr Ala Asn
                295                 300                 305 tca gta ctt gaa cca gga aat tca gaa gta tct tta gta tgt gaa aaa    1498
Ser Val Leu Glu Pro Gly Asn Ser Glu Val Ser Leu Val Cys Glu Lys
            310                 315                 320 ctg tgt aat gaa aaa cta tta aaa aag gct cgt ata cat cca ttt cat    1546
Leu Cys Asn Glu Lys Leu Leu Lys Lys Ala Arg Ile His Pro Phe His
        325                 330                 335 att ttg atc gca tta gaa act tac aag aca ggt cat ggt ctc aga ggg    1594
Ile Leu Ile Ala Leu Glu Thr Tyr Lys Thr Gly His Gly Leu Arg Gly
    340                 345                 350 aaa ctg aag tgg cgc cct gat gaa gaa att ttg aaa gca ttg gat gct    1642
Lys Leu Lys Trp Arg Pro Asp Glu Glu Ile Leu Lys Ala Leu Asp Ala
355                 360                 365                 370 gct ttt tat aaa aca ttt aag aca gtt gaa cca act gga aaa cgt ttc    1690
Ala Phe Tyr Lys Thr Phe Lys Thr Val Glu Pro Thr Gly Lys Arg Phe
                375                 380                 385 tta cta gct gtt gat gtc agt gct tct atg aac caa aga gtt ttg ggt    1738
Leu Leu Ala Val Asp Val Ser Ala Ser Met Asn Gln Arg Val Leu Gly
            390                 395                 400 agt ata ctc aac gct agt aca gtt gct gca gca atg tgc atg gtt gtc    1786
Ser Ile Leu Asn Ala Ser Thr Val Ala Ala Ala Met Cys Met Val Val
        405                 410                 415 aca cga aca gaa aaa gat tct tat gta gtt gct ttt tcc gat gaa atg    1834
Thr Arg Thr Glu Lys Asp Ser Tyr Val Val Ala Phe Ser Asp Glu Met
    420                 425                 430 gta cca tgt cca gtg act aca gat atg acc tta caa cag gtt tta atg    1882
Val Pro Cys Pro Val Thr Thr Asp Met Thr Leu Gln Gln Val Leu Met
435                 440                 445                 450 gct atg agt cag atc cca gcg ggt gga act gat tgc tct ctt cca atg    1930
Ala Met Ser Gln Ile Pro Ala Gly Gly Thr Asp Cys Ser Leu Pro Met
                455                 460                 465 atc tgg gct cag aag aca aac aca cct gct gat gtc ttc att gta ttc    1978
Ile Trp Ala Gln Lys Thr Asn Thr Pro Ala Asp Val Phe Ile Val Phe
            470                 475                 480 act gat aat gag acc ttt gct gga ggt gtc cat cct gct att gct ctg    2026
Thr Asp Asn Glu Thr Phe Ala Gly Gly Val His Pro Ala Ile Ala Leu
        485                 490                 495 agg gag tat cga aag aaa atg gat att cca gct aaa ttg att gtt tgt    2074
Arg Glu Tyr Arg Lys Lys Met Asp Ile Pro Ala Lys Leu Ile Val Cys
    500                 505                 510 gga atg aca tca aat ggt ttc acc att gca gac cca gat gat aga ggc    2122
Gly Met Thr Ser Asn Gly Phe Thr Ile Ala Asp Pro Asp Asp Arg Gly
515                 520                 525                 530
```

```
atg ttg gat atg tgc ggc ttt gat act gga gct ctg gat gta att cga    2170
Met Leu Asp Met Cys Gly Phe Asp Thr Gly Ala Leu Asp Val Ile Arg
            535                 540                 545 aat ttc aca tta gat atg att taatagtcga gcttaattag ctgagcttg         2220
Asn Phe Thr Leu Asp Met Ile
                550
```

<210> SEQ ID NO 6
<211> LENGTH: 553
<212> TYPE: PRT
<213> ORGANISM: Homo sapiens

<400> SEQUENCE: 6

```
Met Gly Gly Ser His His His His His Gly Asp Asp Asp Lys
1               5                   10                  15

Glu Glu Ser Val Asn Gln Met Gln Pro Leu Asn Glu Lys Gln Ile Ala
                20                  25                  30

Asn Ser Gln Asp Gly Tyr Val Trp Gln Val Thr Asp Met Asn Arg Leu
            35                  40                  45

His Arg Phe Leu Cys Phe Gly Ser Glu Gly Gly Thr Tyr Tyr Ile Lys
    50                  55                  60

Glu Gln Lys Leu Gly Leu Glu Asn Ala Glu Ala Leu Ile Arg Leu Ile
65                  70                  75                  80

Glu Asp Gly Arg Gly Cys Glu Val Ile Gln Glu Ile Lys Ser Phe Ser
                85                  90                  95

Gln Glu Gly Arg Thr Thr Lys Gln Glu Pro Met Leu Phe Ala Leu Ala
            100                 105                 110

Ile Cys Ser Gln Cys Ser Asp Ile Ser Thr Lys Gln Ala Ala Phe Lys
        115                 120                 125

Ala Val Ser Glu Val Cys Arg Ile Pro Thr His Leu Phe Thr Phe Ile
    130                 135                 140

Gln Phe Lys Lys Asp Leu Lys Glu Ser Met Lys Cys Gly Met Trp Gly
145                 150                 155                 160

Arg Ala Leu Arg Lys Ala Ile Ala Asp Trp Tyr Asn Glu Lys Gly Gly
                165                 170                 175

Met Ala Leu Ala Leu Ala Val Thr Lys Tyr Lys Gln Arg Asn Gly Trp
            180                 185                 190

Ser His Lys Asp Leu Leu Arg Leu Ser His Leu Lys Pro Ser Ser Glu
        195                 200                 205

Gly Leu Ala Ile Val Thr Lys Tyr Ile Thr Lys Gly Trp Lys Glu Val
    210                 215                 220

His Glu Leu Tyr Lys Glu Lys Ala Leu Ser Val Glu Thr Glu Lys Leu
225                 230                 235                 240

Leu Lys Tyr Leu Glu Ala Val Glu Lys Val Lys Arg Thr Lys Asp Glu
                245                 250                 255

Leu Glu Val Ile His Leu Ile Glu Glu His Arg Leu Val Arg Glu His
            260                 265                 270

Leu Leu Thr Asn His Leu Lys Ser Lys Glu Val Trp Lys Ala Leu Leu
        275                 280                 285

Gln Glu Met Pro Leu Thr Ala Leu Leu Arg Asn Leu Gly Lys Met Thr
    290                 295                 300

Ala Asn Ser Val Leu Glu Pro Gly Asn Ser Glu Val Ser Leu Val Cys
305                 310                 315                 320

Glu Lys Leu Cys Asn Glu Lys Leu Leu Lys Lys Ala Arg Ile His Pro
                325                 330                 335
```

-continued

```
Phe His Ile Leu Ile Ala Leu Glu Thr Tyr Lys Thr Gly His Gly Leu
            340                 345                 350
Arg Gly Lys Leu Lys Trp Arg Pro Asp Glu Glu Ile Leu Lys Ala Leu
        355                 360                 365
Asp Ala Ala Phe Tyr Lys Thr Phe Lys Thr Val Glu Pro Thr Gly Lys
    370                 375                 380
Arg Phe Leu Leu Ala Val Asp Val Ser Ala Ser Met Asn Gln Arg Val
385                 390                 395                 400
Leu Gly Ser Ile Leu Asn Ala Ser Thr Val Ala Ala Met Cys Met
                405                 410                 415
Val Val Thr Arg Thr Glu Lys Asp Ser Tyr Val Val Ala Phe Ser Asp
            420                 425                 430
Glu Met Val Pro Cys Pro Val Thr Thr Asp Met Thr Leu Gln Gln Val
            435                 440                 445
Leu Met Ala Met Ser Gln Ile Pro Ala Gly Gly Thr Asp Cys Ser Leu
    450                 455                 460
Pro Met Ile Trp Ala Gln Lys Thr Asn Thr Pro Ala Asp Val Phe Ile
465                 470                 475                 480
Val Phe Thr Asp Asn Glu Thr Phe Ala Gly Val His Pro Ala Ile
                485                 490                 495
Ala Leu Arg Glu Tyr Arg Lys Lys Met Asp Ile Pro Ala Lys Leu Ile
            500                 505                 510
Val Cys Gly Met Thr Ser Asn Gly Phe Thr Ile Ala Asp Pro Asp Asp
        515                 520                 525
Arg Gly Met Leu Asp Met Cys Gly Phe Asp Thr Gly Ala Leu Asp Val
    530                 535                 540
Ile Arg Asn Phe Thr Leu Asp Met Ile
545                 550

<210> SEQ ID NO 7
<211> LENGTH: 84
<212> TYPE: DNA
<213> ORGANISM: Artificial sequence
<220> FEATURE:
<223> OTHER INFORMATION: Description of artificial sequence:
      synthetic primer HY3-SynF

<400> SEQUENCE: 7
acttggtacc gaaattaata cgactcacta tagggagagg ctggtccgag tgcagtggtg     60
tttacaacta attgatcaca acca                                           84

<210> SEQ ID NO 8
<211> LENGTH: 85
<212> TYPE: DNA
<213> ORGANISM: Artificial sequence
<220> FEATURE:
<223> OTHER INFORMATION: Description of artificial sequence:
      synthetic primer HY3-SynR

<400> SEQUENCE: 8
gtgtctcgag aaaggctagt caagtgaagc agtgggagtg gagaaggaac aaagaaatct     60
gtaactggtt gtgatcaatt agttg                                          85

<210> SEQ ID NO 9
<211> LENGTH: 89
<212> TYPE: DNA
<213> ORGANISM: Artificial sequence
```

```
<220> FEATURE:
<223> OTHER INFORMATION: Description of artificial sequence:
      synthetic primer SSA60M6-NF

<400> SEQUENCE: 9
cacagaattc attaaagagg agaaattaac tatgagagga tcccatcacc atcaccatca    60
cggtgatgac gatgacaaag aggaatctg                                     89

<210> SEQ ID NO 10
<211> LENGTH: 27
<212> TYPE: DNA
<213> ORGANISM: Artificial sequence
<220> FEATURE:
<223> OTHER INFORMATION: Description of artificial sequence:
      synthetic primer SSA60M6-NRev

<400> SEQUENCE: 10
ctaattaaag cttcagcatt ttcaagg                                       27

<210> SEQ ID NO 11
<211> LENGTH: 68
<212> TYPE: DNA
<213> ORGANISM: Artificial sequence
<220> FEATURE:
<223> OTHER INFORMATION: Description of artificial sequence:
      synthetic primer SSA60M5-CF

<400> SEQUENCE: 11
gatactggag ctctggatgt aattcgaaat ttcacattag atatgattta atagtcgcga   60
gccagctt                                                            68

<210> SEQ ID NO 12
<211> LENGTH: 28
<212> TYPE: DNA
<213> ORGANISM: Artificial sequence
<220> FEATURE:
<223> OTHER INFORMATION: Description of artificial sequence:
      synthetic primer SSA60M5-CRev

<400> SEQUENCE: 12
aggcagctct agagcggcgg atttgtcc                                      28

<210> SEQ ID NO 13
<211> LENGTH: 82
<212> TYPE: DNA
<213> ORGANISM: Artificial sequence
<220> FEATURE:
<223> OTHER INFORMATION: Description of artificial sequence:
      synthetic primer HYFPQE

<400> SEQUENCE: 13
acttctcgag aaatcataaa aaatttattt gctttgtgag cggataacaa ttataataga   60
ttcaggctgg tccgagtgca gt                                            82

<210> SEQ ID NO 14
<211> LENGTH: 62
<212> TYPE: DNA
<213> ORGANISM: Artificial sequence
<220> FEATURE:
<223> OTHER INFORMATION: Description of artificial sequence:
      synthetic primer HYRPQE
```

```
-continued

<400> SEQUENCE: 14
gtgtctcgag aaaatgccgc cagcggaact ggcggcaaag gctagtcaag tgaagcagtg       60
gg                                                                      62
```